United States Patent
Reuss et al.

(10) Patent No.: US 7,048,687 B1
(45) Date of Patent: May 23, 2006

(54) LIMITED USE MEDICAL PROBE

(75) Inventors: James L. Reuss, Waukesha, WI (US); Gerhard von der Ruhr, Brookfield, WI (US); Dennis E. Bahr, Middleton, WI (US); Michael T. Larsen, Brookfield, WI (US)

(73) Assignee: OB Scientific, Inc., Germantown, WI (US)

( * ) Notice: Subject to any disclaimer, the term of this patent is extended or adjusted under 35 U.S.C. 154(b) by 262 days.

(21) Appl. No.: 10/361,167

(22) Filed: Feb. 6, 2003

Related U.S. Application Data

(63) Continuation-in-part of application No. 10/045,475, filed on Oct. 22, 2000, now abandoned, which is a continuation of application No. 09/291,769, filed on Apr. 14, 1999, now Pat. No. 6,308,089.

(51) Int. Cl.
  *A61B 5/00* (2006.01)
(52) U.S. Cl. .................. 600/300; 600/338; 600/376
(58) Field of Classification Search .............. 600/300, 600/325, 338, 588, 639, 372–377; 705/2, 705/29
See application file for complete search history.

(56) References Cited

U.S. PATENT DOCUMENTS

| | | | |
|---|---|---|---|
| 5,162,725 A | | 11/1992 | Hodson |
| 5,383,874 A | | 1/1995 | Jackson et al. |
| 5,400,267 A | | 3/1995 | Denen et al. |
| 5,425,362 A | | 6/1995 | Siker et al. |
| 5,651,780 A | | 7/1997 | Jackson et al. |
| 5,720,293 A | * | 2/1998 | Quinn et al. ................. 600/505 |
| 5,850,443 A | * | 12/1998 | Van Oorschot et al. ..... 380/285 |
| 5,860,099 A | * | 1/1999 | Milios et al. ................ 711/103 |
| 5,939,609 A | | 8/1999 | Knapp et al. |
| 5,987,343 A | * | 11/1999 | Kinast ......................... 600/323 |
| 5,991,355 A | | 11/1999 | Dahlke |
| 6,163,715 A | | 12/2000 | Larsen et al. |
| 6,237,604 B1 | | 5/2001 | Burnside et al. |
| 6,266,551 B1 | | 7/2001 | Osadchy et al. |
| 6,298,255 B1 | * | 10/2001 | Cordero et al. ............. 600/372 |
| 6,308,089 B1 | | 10/2001 | von der Ruhr et al. |
| 6,339,715 B1 | | 1/2002 | Bahr et al. |
| 6,708,049 B1 | * | 3/2004 | Berson et al. .............. 600/323 |
| 2002/0095077 A1 | | 7/2002 | Swedlow et al. |

(Continued)

FOREIGN PATENT DOCUMENTS

DE 19825754 A1 1/1999

(Continued)

OTHER PUBLICATIONS

Cammack T. Statement to the Food & Drug Administration, Public Hearing on Bar Coding, Friday, Jul. 26, 2002 Bethesda MD; NIH, Jul. 26, 2002 pp. 1-3.

(Continued)

*Primary Examiner*—Eric F. Winakur
(74) *Attorney, Agent, or Firm*—Reinhart Boerner Van Deuren sc

(57) ABSTRACT

A limited use medical probe is disclosed, including a memory for maintaining a use value. The medical probe is coupled to a medical device that inhibits its function when the use value reaches a predetermined threshold value, preventing improper use of the probe. The probe memory may also store identification, usage, and clinical data. A probe auto-identification function, a probe re-identification function and a probe functional test sequence are disclosed for the medical probe. After use, a reprocessing step may reset the probe memory, permitting further probe use.

19 Claims, 9 Drawing Sheets

U.S. PATENT DOCUMENTS

2002/0095078 A1    7/2002    Mannheimer et al.

FOREIGN PATENT DOCUMENTS

| WO | WO97/29678 | 8/1997 |
|----|------------|--------|
| WO | WO 99/49313 | 9/1999 |

OTHER PUBLICATIONS

Kohn T. Corrigan J. Donaldson M (ed). To err is human: Building a safer health system. Institute of Medicine, National Academy Press; 1999, pp. 23-38, Washington, D.C..

DS2480 Serial 1-Wire™ Line Driver. Dallas Semiconductor, Inc.; 1999, pp. 1-26.

DS2502 1 kbit Add-Only Memory. Dallas Semiconductor, Inc.; 1999, pp. 1-22.

Labeling Recommendations for Single-Use Devices Reprocessed by Third Parties and Hospitals; Final Guidance for Industry and FDA. US HHS FDA CORH, Rockville MD; Jul. 30, 2001, pp. 1-9.

Premarket Guidance: Reprocessing and Reuse of Single-Use Devices; Draft Guidance for Industry and FDA Staff. US HHS FDA CORH, Rockville MD; Jun. 1, 2001, pp. 1-12.

* cited by examiner

LIMITED USE MEDICAL PROBE

This application is a continuation-in-part of application Ser. No. 10/045,475, filed Oct. 22, 2001 now abandoned, which is a continuation of application Ser. No. 09/291,769, filed Apr. 14, 1999, which is now issued as U.S. Pat. No. 6,308,089 on Oct. 23, 2001, the disclosures of which are incorporated herein by reference.

BACKGROUND OF THE INVENTION

1. Field of the Invention

The present invention relates generally to medical probes, including sensor devices and methods for measuring clinical physiological parameters including vital signs. More particularly, the invention is concerned with a medical system that limits the use of an associated medical probe according to usage criteria to prevent misapplication, overuse and potential failure, including auto-identification of the probe, addressing the problem of re-identification when the connection of a medical probe to the medical device is interrupted during use. The invention describes a medical reprocessing system that performs reprocessing (utilization history review, functional testing, and authorization for reuse) of a previously used medical probe. Usage criteria may include duration and/or number of uses, shelf or warranty life, and/or compatibility of the medical probe with the patient and/or selected medical probe function(s).

Medical probes include devices that are inserted into a body cavity or under the skin of a patient in order to perform therapy or monitoring. Such probes, including devices to view or scan tissue, or monitor biological parameters, are well known in the art. A sensor device typically comprises a housing including at least one sensor such as a pressure sensor; a light emitting device and associated detector comprising a pulse oximetry sensor; an ECG sensor; or other vital sign monitoring device; plus a means of conveying information from the sensor device to a caregiver. One particular example of a medical sensor device is fetal sensor, including external sensors placed on the maternal abdomen and internal sensors placed through the birth canal onto a part of the fetus. An example of an internal fetal sensor is a fetal pulse oximetry sensor, such as described in U.S. Pat. No. 5,425,362 to Siker et al. The sensor described therein is inserted past the cervical os into the uterus of the mother to non-invasively monitor the condition of a fetus, a mother, and/or a placenta.

One problem associated with known medical probes is that they have a limited life span. Probes are prone to wear through repeated use or through extended use over a period of time, and through cleaning and sterilization processes. Problems associated with such overuse include spurious readings as internal wires and connectors become loose. More importantly, probes that are used repeatedly or over an extended period of time are prone to break. Once such an incident occurs, it is often difficult to determine when the probe failed, or to track the cause of such an occurrence. Furthermore, medical probes often have a limited shelf life or warranty period, i.e., the period of time after manufacture during which they are guaranteed to function properly. An out-of-date medical probe may fail to function to manufacturer's specifications, posing a health risk to the patient.

To prevent these problems, medical clinicians may limit the number and duration of uses of a given probe through an equipment log or other manual system. While such systems may be effective in certain circumstances, they rely heavily on manual records, which are time-consuming and difficult to maintain, particularly since the cooperation of a number of clinical personnel is required. In busy hospital settings, and especially in emergency situations, such systems are difficult to manage and are easily overlooked or ignored.

The prevalence of medical errors, some related to misuse of medical devices, has been detailed in the 1999. Institute of Medicine report "*To Err is Human*," chapter 2, ISBN 0-309-06837-1. Interest in reducing medical errors has motivated an initiative to uniquely identify all drugs and medical devices, to assist in prevention of medical errors by correlating the drug or device with the patient's identification and intended procedure. In response to a U.S. Food & Drug Administration (FDA) suggestion to use bar codes under the Universal Product Numbering (UPN) system, the Advanced Medical Technology Association (AdvaMed), a medical device industry association, has suggested in a statement to employ generic "auto-identification" methods, which could include RF or other electronic means as an alternative to bar code technology. (Statement to the Food & Drug Administration by T. Cammack on Jul. 26, 2002.)

A particular class of medical probe is the single-use device (SUD). A device may be designed as an SUD by the manufacturer for several reasons, including: the risk of cross-contamination between patients; because some key component (for example, a battery or reagent) is sufficient only for one use; due to difficulty in the cleaning and sterilization to permit reuse; or due to the prohibitive cost of producing a device durable enough to be reused. Despite manufacturers designations, clinical institutions and third-party services sometimes choose to refurbish SUDs and reuse them. This practice has become increasingly common as clinical institutions experience financial pressures, since a SUD may be refurbished at a substantial discount from the retail price of a new one.

Typically, refurbishing of an SUD entails cleaning, inspection, sterilization, replacement of worn or exhausted components, and re-validation for safety and efficacy. The practice is so widespread that regulatory bodies in the United States and around the world have instituted legislation to limit and/or monitor the reuse of SUDs. The FDA documents "Premarket Guidance: Reprocessing and Reuse of Single-Use Devices" (Jun. 1, 2001) and "Labeling Recommendations for Single-Use Devices Reprocessed by Third Parties and Hospitals" (Jul. 30, 2001) have provided guidance with respect to compliance with the U.S. regulatory requirements. One aspect of regulation that is being emphasized is the need for good record keeping in tracking the history of use of an SUD, including how long and in what fashion the SUD was used.

The manufacturer of a medical device also faces the possibility of counterfeiting. In some cases, an unscrupulous manufacturer seeks to avoid paying licensing fees for proprietary technology used in the device. Even if misappropriation of intellectual property is not involved, a second manufacturer may seek to undercut the price of the original device by producing it with less expensive components, labor, or both. In any case, when a lower-quality device is used in a medical application, patient safety becomes the issue. In particular, SUDs or limited-use devices are generally designed to work in conjunction with a medical monitor. It is important to ensure that every medical sensing device utilized with the monitor is designed and calibrated to work properly with it.

Several partial solutions to the problem of controlling use of a medical probe have been proposed. U.S. Pat. No. 5,991,355 to Dahlke proposed a simple identification and counting system associated with an electrophysiology sensor for the purpose of limiting reuse of said sensor. However, the method entails simple counting of uses, without support for usage limitation based upon utilization time; nor does it include device identification.

In U.S. Pat. No. 5,400,267 to Denen et al., a medical device (electro-surgical knife) with an embedded non-volatile memory component is described. The memory stores utilization limits and operating parameters. The invention permits the system attached to the device (in that case, a power supply) to (a) configure itself for appropriate operation with the device, and (b) disable the device after some operational limit is exceeded. The need for re-identification of the medical device if the connection with the system is broken is disclosed. This is intended to prevent the system from counting any pause in use less than a preset period as a new use. However, the patent proposes only to store the current time in the medical device during use, without considering how to prevent this data from being manipulated to prevent the system from detecting the occurrence of a new use.

U.S. Pat. No. 6,237,604 to Burnside et al. proposes usage control based upon cycles or usage time, but fails to address the management of legitimate medical probe reprocessing.

U.S. Patent Application 2002/0095078 A1 to Mannheimer et al. specifically relates to pulse oximetry sensor reuse, supporting limits on number of sterilization cycles or warranty expiration date. None of these patents or applications addresses the need for security features or security functions to prevent product counterfeiting or tampering with the usage control method.

Similarly, the non-medical sensing device for attachment to a measurement instrument described in U.S. Pat. No. 5,162,725 to Hodson et al. offers no provision for establishing the authenticity of the sensing device (e.g., probe) when it is coupled to the instrument. That is, no means is suggested to solve the problem of preventing use of a counterfeit sensing device, that is constructed to include similar calibration and identification data.

The prevalence of electronic technology in the world makes it relatively easy to counterfeit the memory devices proposed for control of reuse with modest effort. Potentially, a medical device could be reprocessed by replacing the memory component with a copy made from an unused original. The counterfeit memory could be placed in a reusable adapter used in conjunction with an expired medical probe. Alternatively, an entire counterfeit sensing device could be manufactured that was indistinguishable with respect to the memory component or its content.

The U.S. Health Insurance Portability and Accountability Act of 1996 expressed the need for protection of privacy in storage and transfer of healthcare information. This is detailed in the Federal Register, Vol. 63 No. 155, 45 CFR Part 142, Security and Electronic Signature Standards.

Another application of a memory component associated with a medical probe is storage of patient data and patient identification data, disclosed in related inventions U.S. Pat. No. 6,308,089 to von der Ruhr et al. and continuation application Ser. No. 09/291,769. The aforementioned patent reveals the use of encryption to permit the secure storage of data related to the usage of a medical probe, including one or more of its identifying data, duration of use, number of uses, or time and date stamp of use.

U.S. Patent Application 2002/0095077 A1 to Swedlow et al. discloses storage of patient identification data, pulse rate, and oxygen saturation values, etc., in a pulse oximetry sensor. However, a means for secure storage and data transfer to ensure data integrity and privacy is not disclosed.

Secure data storage and transfer in automated systems can be achieved utilizing a physical security method and/or an algorithmic security method. The physical security method relies upon the use of a physical object which might be difficult to bypass or forge, such as a door requiring a physical key to unlock it, whereas an algorithmic security method might rely upon the use of secret data, such as a password or personal identification number (PIN) entered into a keypad. In biometrics, the physical "key" is some characteristic physical property of the authorized user, such as a fingerprint, retinal image, voiceprint, and so forth. Combining multiple techniques of using physical and/or algorithmic security methods offers the best hope of providing a secure authentication method. This strategy can be applied to the problem of securing the data in a limited use medical sensor.

The more usage, calibration, and clinical data that is to be stored in a medical probe, the more important it becomes to utilize an efficient storage method. Data compression, particularly lossless data compression, is an encoding method to store more data in less physical memory without information loss. Error detection and correction can also be part of the method. The encoding of data in a medical probe should preferably address the needs of data security, integrity, and storage efficiency.

There remains, therefore, a need for a medical system that can automatically control the use of a medical probe through enforcement of usage criteria. Such usage criteria would include: limiting the duration and/or number of uses of the probe to a predetermined limit value; limiting use of the probe to a shelf life or warranty period; permitting use of the medical probe only after validation of the combination of medical probe, patient and procedure; and limiting access to patient data stored within the medical probe to ensure patient privacy. Preferably, the medical system would also provide additional functions, such as data compression, error checking, time and date stamping, and security checking, that would facilitate this usage control, as well as regulated reprocessing of medical probes prior to reuse. Data stored in the medical probe, related not only to probe usage but also patient identity and condition, should be held in a secure fashion.

It is therefore an object of the invention to provide a medical system that can limit the number of times a medical probe is used.

It is another object of the invention to provide a medical system that can limit the duration of the use of a medical probe.

It is yet another object of the invention to provide a medical system that can limit the use of a medical probe to a certain shelf life or warranty period.

It is still another object of the invention to provide a medical system that provides a time and date stamp to identify when the therapeutic or monitoring operation performed by the medical system in conjunction with the medical probe took place.

It is a still further object of the invention to provide a medical system that provides an auto-identification function to validate proper use of a medical probe with a medical device on a particular patient for a requested therapy or monitoring function.

It is another object of the invention to provide a medical probe that can store data regarding the duration of use of the probe.

It is yet another object of the invention to provide a medical probe that can store data regarding the number of times the probe has been used.

It is still another object of the invention to provide a medical probe that can store a usage limit on the number of times or duration of time the probe may be used.

It is yet another object of the invention to provide a medical probe than can store data regarding the reprocessing of the medical probe for subsequent reuse.

It is a yet further object of the invention to provide a medical system in which identifying data for the medical probe and other medical devices is stored in each.

It is another object of the invention to provide a medical system in which a medical device can re-identify a medical probe after an interruption in use, to prevent the interruption from being construed as a new use.

It is still another object of the invention to provide a medical system that includes a security function for verifying the identity of an attached probe.

It is yet another object of the invention to provide a medical system that includes a security function to prevent tampering with data stored in the probe.

It is a still further object of the invention to provide a medical system that employs a data encoding system including encryption as an algorithmic security method when storing data in the medical probe as part of a security function.

It is another object of the invention to provide a medical system that includes a probe functional test sequence.

It is another object of the invention to provide a medical reprocessing system that can read the usage data in an attached medical probe.

It is a yet further object of the invention to provide a medical reprocessing system that can store reprocessing data in an attached medical probe.

It is still another object of the invention to provide a medical reprocessing system than can store usage control data in an attached medical probe, indicating the number of reuses and/or duration of reuse of the probe to be permitted subsequent to reprocessing.

It is a still further object of the invention to provide a medical reprocessing system that can detect and delete patient data from an attached medical probe.

It is yet another object of the invention to provide a medical reprocessing system that includes a security function for verifying that reprocessing of an attached medical probe is permitted.

It is another object of the invention to provide a medical reprocessing system that includes an authorization function to prevent reprocessing of an attached medical probe without obtaining authorization in a secure fashion from a licensing or regulatory party.

SUMMARY OF THE INVENTION

In one aspect, the present invention is a medical probe that includes at least one effector or sensor device and a probe memory for maintaining use data, e.g., use values, about usage of the probe. The probe memory can include use values such as data regarding the number of times the medical probe has been used, the duration of each use, the total duration of use in conjunction with one or more medical devices, and other data regarding the duty cycle of usage of the medical probe. Other use values, include the date and time of a given use of the probe, the date and time when a given condition occurred, product identity, clinical data such as patient or doctor data, and other medical data can also be stored in the memory storage location of the sensor device. Certain contents of the probe memory are processed by an encoding system including encryption and stored in encrypted form to facilitate security functions as well as maintain confidentiality of patient data. The medical probe preferably contains identifying data (such as a lot number or unique serial number) which is electronically readable, that can be used in a security function to identify the device and prevent tampering with the use data. The serial number can serve an auto-identification function for reducing medical errors.

The medical probe, capable of communicating with external devices, is coupled to a medical device to provide a medical system. The medical device, through communications with the medical probe, applies usage criteria to limit use of the medical probe. Usage criteria include data limiting the use of the medical probe. The medical device determines usage of the medical probe and limits the total use of each medical probe to a limit value by preventing use beyond a predetermined usage limit. The usage limit, as noted above, can be based on one or more of the following usage criteria: total number of uses, total duration of use, shelf life, warranty period, regulatory guidelines or licensing agreement. Usage criteria applied by the medical device may further include validating that the combination of the medical device, patient, and intended therapy or monitoring are correct.

The use of a medical probe may be interrupted without constituting a new use, i.e., use resumes on the same patient without intervening use on another patient after a period of interruption sufficiently short to not require changing the use value. A probe re-identification method is included in the invention to prevent unnecessary reduction of the medical probe's intended utility during the course of its useful life.

The medical device, in conjunction with the medical probe, provides a probe evaluation including a security function for verifying the identity of the medical probe. Preferably, the security function operates on internal serial numbers and encryption keys to ensure that the proper probes are coupled to the medical device, that the internal use data has not been tampered with, and to verify communications between the medical probe and medical device. An auto-identification function is advantageously included in the probe evaluation.

The medical device may include a functional test sequence applied to the medical probe prior to use. Preferably, the medical device can determine that the medical probe is working within normal operating parameters by performing the functional tests. For effectors, the testing may include a determination that power outputs are within expected values. For sensors, the testing may evaluate sensitivity and signal to noise ratio. Expected test results based upon design testing, factory calibration, or previous functional tests may be stored in the medical device and/or the medical probe for comparison purposes.

The medical system can also provide a series of product identity functions, as well as storing the identifying data (e.g., serial numbers) for the equipment used in a given medical procedure. The stored data can further include a date and time stamp, identifying data regarding the medical personnel involved in a monitoring procedure, identifying data about the patient, clinical data, and other data related to clinical use. The stored data can further include data related to reprocessing of the medical probe, such as personnel and facility identification, data and time of reprocessing, and authorization by a licensing or regulatory party. Once again, in a preferred embodiment an encoding system including encryption is utilized for data compression, error checking, and to ensure authenticity and to protect patient confidentiality.

Subsequent to use of the medical probe past usage limits, the medical probe may optionally be attached to a medical reprocessing system. The medical reprocessing system communicates with the probe memory of the medical probe, utilizing the data therein to direct reprocessing and maintain a database regarding the history of the probe. An optional authorization step by a licensing or regulatory party may further qualify the decision-making. If reprocessing is successful, the contents of the probe memory of the medical probe is amended or modified to permit further use; if reprocessing is unsuccessful, the medical probe is rendered inoperable.

The medical probe preferably includes a probe memory such as a low-power integrated circuit. In one preferred embodiment, the probe memory is an add-only memory (AOM) that is embedded in the medical probe. The AOM preferably includes a tamper-proof serial number and medical equipment manufacturer identification field written by the AOM manufacturer as a built-in security function to prevent counterfeiting of the AOM; a field of identifying data and usage criteria data written by the medical probe manufacturer at the time of probe production; a field of use values written by the medical system in the course of clinical use; and a field of reprocessing data written by the medical reprocessing system.

In one highly preferred embodiment of the invention, the medical monitoring system comprises a fetal sensor for monitoring oxygen saturation in the blood of a fetus while in the womb. The probe memory is embedded in the connector used to attach the medical probe to the medical device, which is a fetal pulse oximeter.

Other advantages and features of the invention, together with the organization and manner of operation thereof, will become apparent from the following detailed description when taken in conjunction with the accompanying drawings wherein like elements have like numerals throughout the drawings.

DETAILED DESCRIPTION OF THE PREFERRED EMBODIMENT

Figure 1:
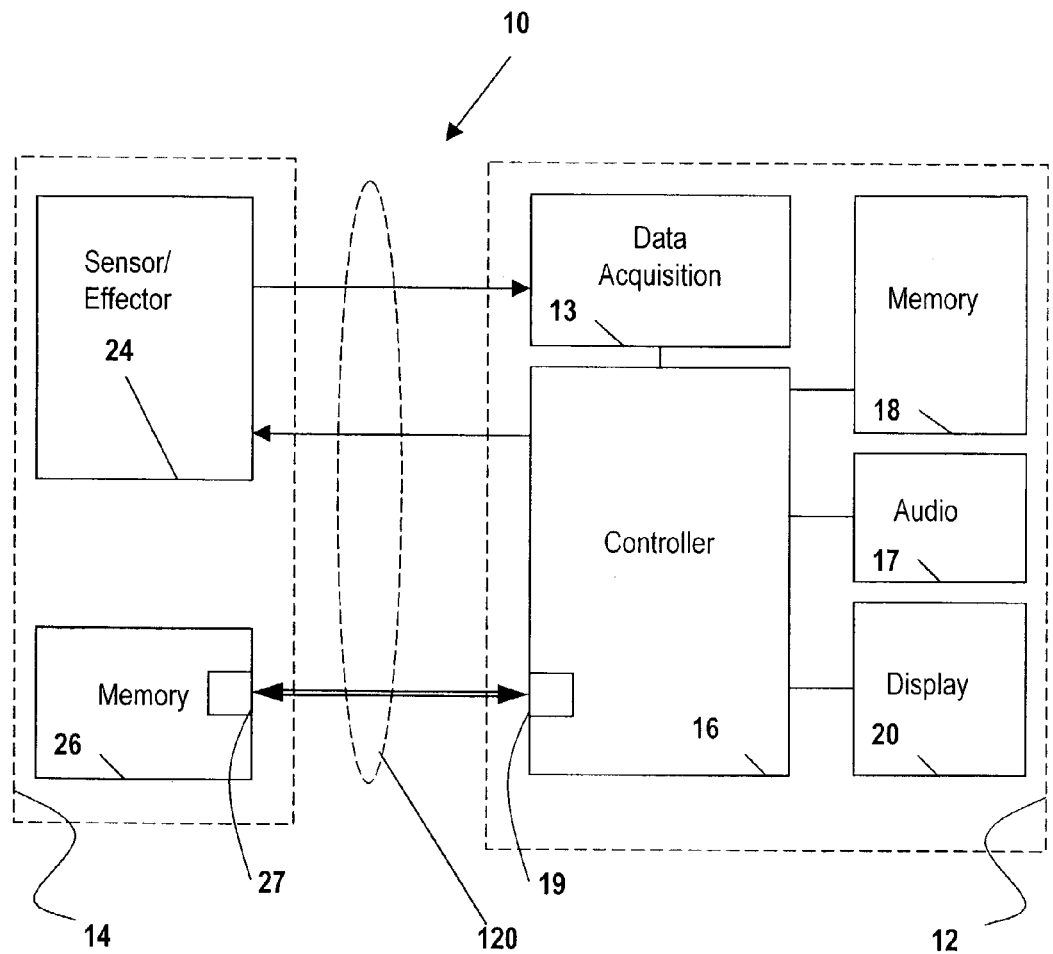
FIG. 1 is a block diagram of a medical monitoring system constructed in accordance with the present invention.

Referring now to FIGS. 1–7, and more particularly to FIG. 1, a block diagram of a medical system constructed in accordance with the present invention is shown at 10. Generally, the medical system 10 comprises a medical device 12 and a medical probe 14.

Preferably, the medical device 12 includes a data acquisition device 13, a controller 16, an audio output device 17, at least one memory 18, and a display 20. Preferably, the controller 16 includes a device (host) communications port 19 such as a serial communications port or other digital communication means. The controller 16 is preferably a microprocessor, but can comprise a micro-controller or various other types of control devices. The memory 18 preferably comprises a RAM (read/writable) device and an EPROM (read only) device, but other known types of memory devices may be used without departing from the invention. Preferably, the medical device will include non-erasable memory components for storing a serial number, as will be described more fully below. In some applications, the controller 16 may include a memory 18 as part of the integrated circuit, thereby eliminating the need for external memory devices.

Hereafter where reference is made to writing a message to the display 20 of the medical device 12, it will be understood that this can refer to a text message on an alphanumeric or graphic display. Alternatively, the display 20 may comprise a bank of indicator lights or LEDs that provide similar data.

The medical probe 14 generally comprises an effector/sensor 24, a probe memory 26, and an external connection 120 configured for communicating and transfeffing data between the medical device and the probe. An effector may comprise any of a number of therapeutic devices for cutting, delivering electrical, acoustic, or RF energy, etc. A sensor may include pressure sensors, ECG sensors, EEG sensors, temperature sensors, oxygen sensors, ultrasound transducers, chemical sensors, etc. The selection of effectors/sensor(s) 24 and associated hardware used in the medical system 12 is dependent only on the type of therapeutic or monitoring functions to be performed without reference to other aspects of the invention. The connection 120 between medical probe 14 and medical device 12 is preferably electrical in nature, but may alternately be fiber optic, free-space optical (e.g., infrared), or radio frequency.

Figure 2:
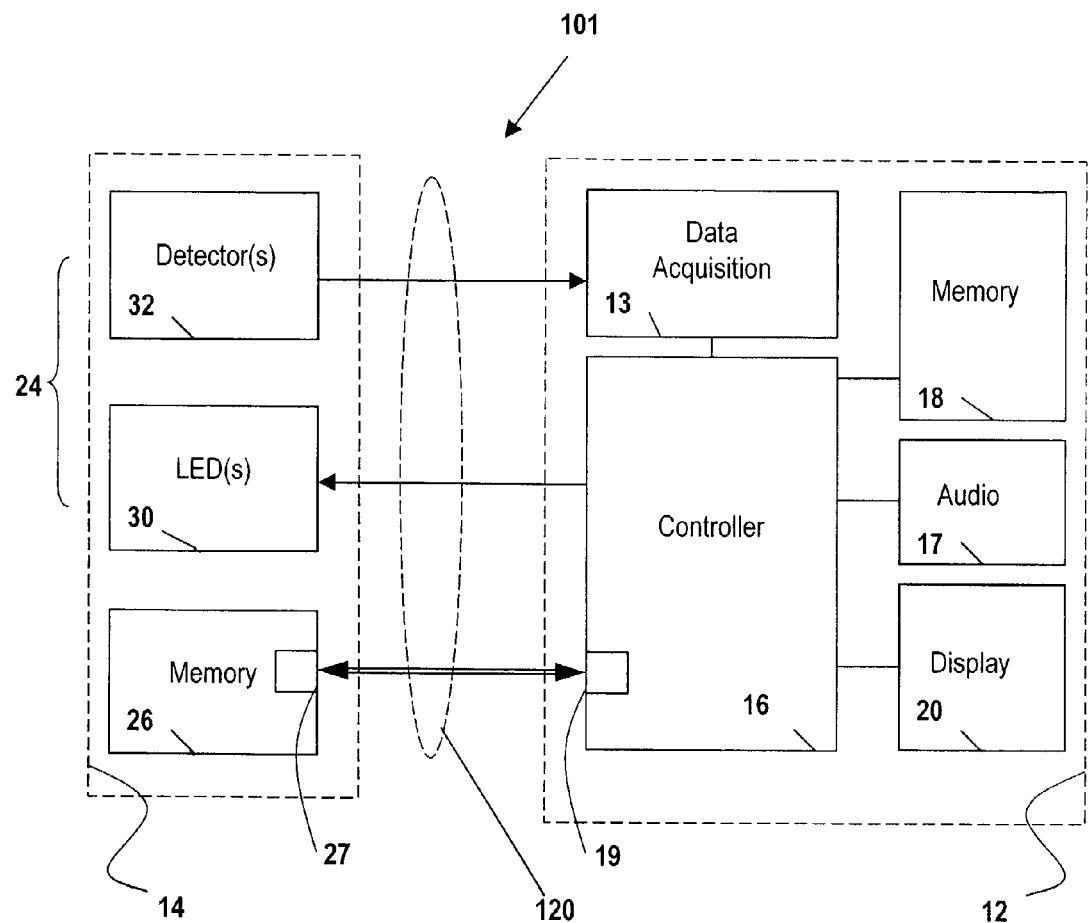
FIG. 2 is a block diagram of a medical monitoring system constructed in accordance with a preferred embodiment of the present invention.

In FIG. 2, a preferred embodiment of the medical system 10 is a pulse oximeter 101 having a medical probe 14 and a medical device 12. The medical probe 14 and medical device 12 are as previously described herein except that the effector/sensor 24 includes light emitting device(s) 30 and associated detector(s) 32. In a preferred embodiment, the light emitting devices 30 are light-emitting diodes (LEDs).

Data used in the medical system 10, 101 is preferably in a digital electronic format.

Referring now to FIGS. 1 and 2, the probe memory 26 can comprise a number of various known devices including microcontrollers or microprocessors, EPROMS, EEPROMS, or application specific chips. These devices provide a memory location for maintaining data concerning use of the medical probe 14. The probe memory 26 also includes probe communications port 27 such as a serial communications port or other digital communication means. In some applications, separate communication devices may also be included. Preferably, more sophisticated devices that provide functions such as product identity, security checking, and date and time stamping are used.

The security function includes a physical security method and/or an algorithmic security method. The physical security method and/or algorithmic security method may be used in the storage and transfer of data from the probe memory 26 to the medical device 12. In a preferred embodiment of a physical security method, the probe memory 26 is a memory that can be written only once, such as a PROM or EPROM, providing physical security of the data (i.e., 0's can be rewritten as 1's, but not vice versa). In one highly preferred embodiment of the invention, the probe memory comprises an add-only memory (AOM) which has pre-programmed serial number and medical equipment manufacturer data. An add-only memory provides physical security of the already-written data (i.e., prevents remaining 0's in the written data from later being rewritten as 1's).

Algorithmic security methods involve the use of an encoding system including algorithms to verify the integrity of data, e.g., the cyclic redundancy check (CRC); and algorithms to prevent unauthorized access to the data, e.g., encryption. The algorithms may be implemented as software in a processor, or as a hardware circuit, without changing the intent. Preferably, the encoding system will also accomplish lossless compression of the data to reduce the physical storage requirements of the memory.

Other highly preferred devices that can be used for the probe memory 26 include a token card chip that includes both memory storage and security functions, and EEPROMS with built-in CRC and serial number functions. These preferred devices will be described more fully below. (The use of a token card chip for limiting the use of a medical probe is disclosed in Applicants' U.S. Pat. No. 6,308,089 and pending patent application Ser. No. 10/045,475, the disclosures of which are herein incorporated by reference.)

As noted above, an important function of the probe memory 26 is to store data regarding the duration of use of the medical probe 14, and/or to maintain a history of the number of uses of the medical probe 14. This data will hereinafter be referred to as "use value". The probe memory 26 can also store data such as, but not limited to, date of manufacture, warranty information, security data such as serial numbers or lot numbers, product identity and encryption keys, history data such as the identity of medical workers (caregivers) involved in the monitoring process (procedure), patient data including physiological data collected by the sensor (or effector) 24 itself or transferred from another source via the medical device 12, and other types of data. The serial number can serve an auto-identification function when combined with patient, procedural, and caregiver identifying data by the medical device 12 to determine if a valid combination has been made, as described below. In alternative embodiments, the probe memory 26 may also be used to store as data the results of functional test routines and other product testing data.

The memory 18 of the medical device 12 preferably also includes data such as identifying data (e.g., serial numbers) identifying the monitoring device and encryption keys, that can be used to verify communications and identify devices as will be described below. To provide physical security, this data is preferably stored in non-erasable memory components (not shown) such as a read-only memory (ROM). The memory 18 preferably also stores other data, such as troubleshooting and calibration data to provide a cross check against the data stored in the medical probe 14.

Identifying data for the medical probe 14, usage criteria, and one or more encryption keys can also be stored in the probe memory 26 at the time of manufacture of the medical probe 14. The identifying data is preferably a serial number used to uniquely identify a specific probe, as well as to identify the type of probe. In some embodiments, identifying data may consist of a production lot number instead of a unique serial number. Preferably, data relating to the date of manufacture, revision codes, and calibration data, determined by the type of probe or its specific assembly, can also be stored in the probe memory 26 at the time of its manufacture.

At the time of manufacture of the medical probe 14, data representing one or more usage limit(s) representing either a count (number of times of medical probe 14 use) or time duration (length of time medical probe 14 is used) can be written into the probe memory 26. Alternatively, the usage limit(s) may be embedded in the memory 18 of the medical device 12. In addition to or in place of these usage limit(s), data such as the date of manufacture or reprocessing stored in the medical probe 14 may serve as the basis for limiting probe use based upon shelf life or warranty period (stored in either the probe or the device). In this case, a real-time clock must be maintained in either the medical probe 14 itself, or the medical device 12.

Figure 3A:
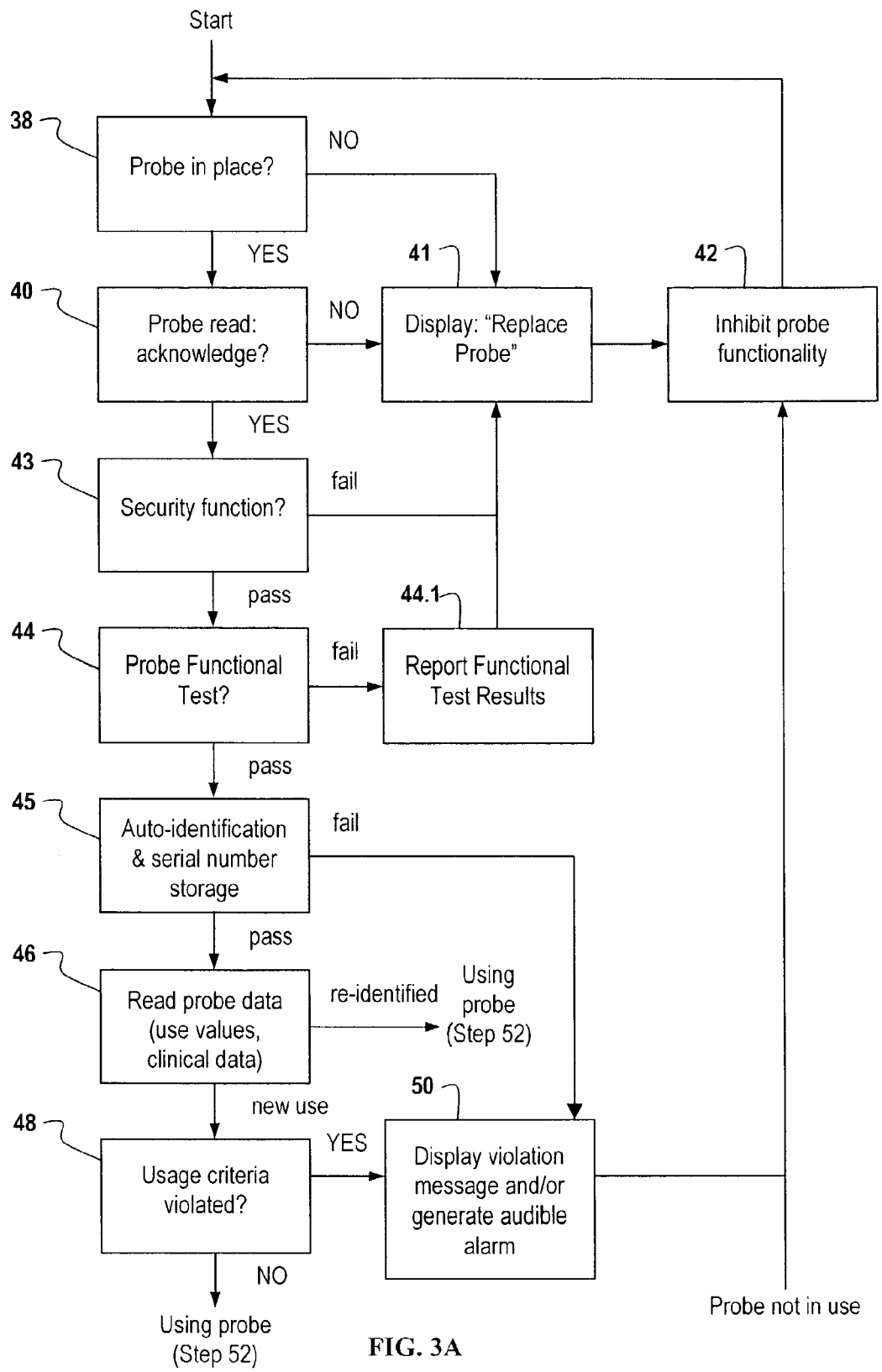
FIG. 3 is an operational block diagram of the medical monitoring system of FIGS. 1 and 2 of the present invention.
Figure 3B:
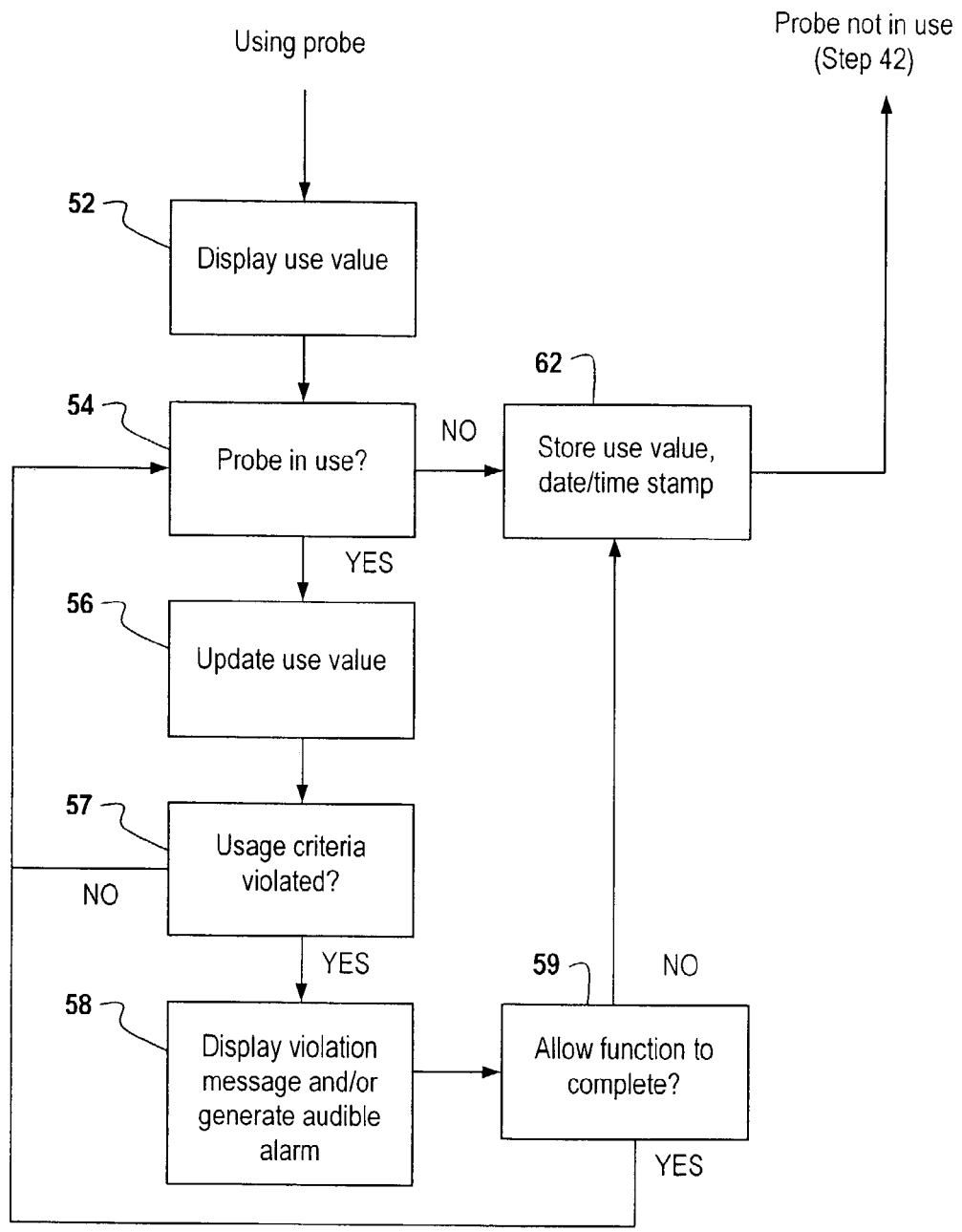
Figure 3C:
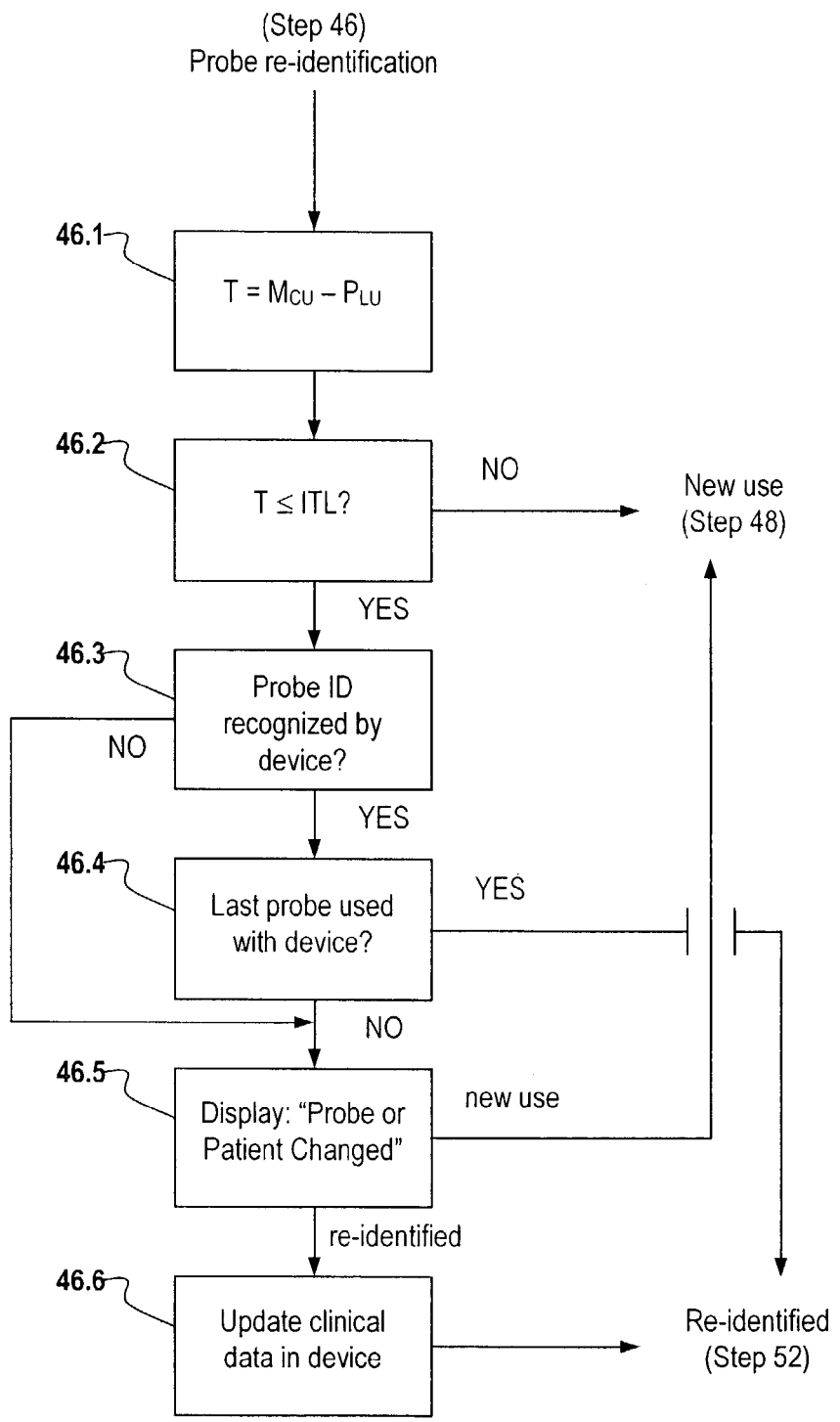

FIG. 3 (3A, 3B, 3C) is an operational block diagram illustrating a method of limiting use of medical probe 14 in the medical systems 10, 101 shown in FIGS. 1 and 2, respectively. FIGS. 3A, 3B show Steps 38–62. FIG. 3C illustrates the detail of Step 46. The method preferably includes use of a security function, a probe auto-identification/re-identification function, and a probe functionality test sequence. It will be understood in the following description that the "reading" and "writing" of the memory storage device 26 in the medical sensor 14 encompasses, in a preferred embodiment, applying an encoding system with encryption to secure the data when reading from and writing to the memory.

Processing commences when a medical probe 14 is detected as attached to the medical device 12 in Step 38. To ensure a proper connection and verify that a proper medical probe 14 is coupled to the medical device 12, in Step 40 an initial query is transmitted to the medical probe 14. After transmitting such a query to the medical probe 14, the medical device 12 waits for an acknowledgement (signal or message) from the medical probe 14 prior to performing any further steps. This query and acknowledge sequence (Step 40) verifies that the probe memory 26 is receiving power and can communicate with the controller 16 in the monitoring device 12 through a serial or other communications link.

If, in Step 40, no acknowledgment is received, the controller 16 of the medical device 12 will determine that the medical probe 14 currently attached is an incorrect medical probe or is not functional. Preferably, in Step 41 the controller 16 will provide a message to the display 20, such as "Replace Probe", and/or will emit an audible alarm (medical alarm) to the audio output 17, and in Step 42, the controller 16 will inhibit functions related to the medical probe 14 until a suitable one is attached to the medical device 12. Although a query and acknowledge step, Step 40, is shown, it will be apparent to one of ordinary skill that the step may not be required in all applications. Furthermore, the ability to perform this step will depend on the functionality of the component chosen as the probe memory 26 in the medical probe 14.

Besides evaluating the correctness of a medical probe to the medical device and the immediate functionality via Step 40, the method of the present invention in Step 43 further ensures that a proper medical probe 14 is coupled to the medical device 12, to secure communications between the medical probe 14 and the medical device 12, and to prevent tampering with the use value and/or usage limit(s) stored in the probe memory 26. In Step 43 the medical system 10 of the present invention preferably uses the serial numbers and encryption keys described above to provide a security function. Each serial number is preferably transmitted from one to the other i.e., from the medical probe 14 to the medical device 12, and from the medical device 12 to the medical probe 14, in encrypted form. The data in the keys and algorithms required by the encryption aspect of the data encoding system to decrypt the transmitted data are preferably stored in a secure fashion within each device (medical probe 14 and/or medical device 12), or transmitted in a secure fashion. Suitable encryption algorithms for encoding systems are well known, including symmetrical key encryption systems, and asymmetrical key encryption systems, such as, but not limited to, public key encryption. A cyclic redundancy code (CRC) calculation and check is also commonly used to validate integrity of transmitted data. A data encoding system serves not only to verify transmissions and validate data, but can also determine a signature of the transmitted data, thereby identifying the specific sending device (medical probe 14 and/or medical device 12). It will be apparent that some data encoding systems designed for data compression will also adequately ensure data encryption for a security purpose.

Preferably, the medical device 12 cannot access data relating to the use value(s) and/or usage limit(s) stored in the probe memory 26 until the validity of the medical device 12 is validated by the security function(s) in the medical probe 14. Step 43 can be accomplished directly, by processing in the probe memory 26, or indirectly, by employing a security key found only inside a valid medical device 12 when applying the encryption algorithms of the data encoding system to the contents of the probe memory 26. If the security function fails to validate the medical probe 14, a message is preferably written to the display 20 of the medical device 12 and/or an audible alarm is generated by the audio output 17 (Step 41), and the controller 16 inhibits functions related to the medical probe 14 until a new one is attached (Step 42).

Preferably, in Step 43 the security function also validates the memory component 26 integrity by verifying that the contents of the memory component 26 have not been tampered with before proceeding. Besides successful decryption in Step 43, further steps at validation of memory integrity include examination of validity of date and time stamps, and possibly lookup of the serial number of the medical probe 14 in a database stored inside of or in communications with the medical device 12, as part of the probe auto-identification function.

In alternative embodiments, as part of probe evaluation, a functional test sequence is invoked in Step 44, wherein each of the effector/sensor(s) 24 of the medical probe 14 is activated to verify functionality. For example, in a pulse oximeter sensor the functional tests may include correlation of a response of the detector 32 with a drive, or electrical current level, of the LED 30 for the plurality of LED(s) illuminating the detector 32. In Step 44.1, the results of these functional tests can be reported by storing the results in internal memory 18 of the medical device 12, writing the results to the probe memory 26 in the medical probe 14, writing the results to the display 20 for immediate review by medical personnel, or a combination of the above.

If the probe fails the functional tests, the method defaults to Step 41 and a violation message, describing the functional test failure is described, and a message indicating "Replace Probe" is written to display 20 and/or an audible alarm is generated by audio output 17. Functions of the medical device 12 related to this medical probe 14 are inhibited until another probe is connected to the medical device 12.

Upon completion of the security function of Step 43 and functional tests of Step 44, the identifying data of the medical probe 14 (e.g., the serial number) is preferably stored in Step 45 in the memory 18 of the medical device 12 for identification purposes. The identifying data of the medical device 12 is preferably stored in the probe memory 26 to provide a cross check, as will be described more fully below.

This exchange of identifying data is the basis for the probe auto-identification function, considered to be part of the usage criteria testing. In Step 45, the medical device 12 can use the probe's identifying data read from the medical probe 14 to determine the type of probe being used. For example, if the medical system 10 is used for fetal pulse oximetry, the medical device 12 can determine if the attached medical probe 14 is a fetal monitoring sensor, versus a sensor device more commonly used with adults, such as a finger sensor. Using this information, the medical device 12 can adjust parameters and algorithms to match the specific functional requirements of the medical probe 14. Such parameters for sensor devices 24 include dynamic range, signal processing characteristics, probe calibration, medical alarm limit values, display content and format, trend data storage content and format, and network communications content and format. In a pulse oximeter sensor, the parameters may include LED emission characteristics (e.g., center wavelength(s) and spectrum width(s)), calibration table (normalized ratio versus $SPO_2$ value), and detector characteristics.

Another feature of the auto identification function of Step 45 uses the identifying data of the medical probe 14, in conjunction with information about the configuration of the medical device 12 and patient data available in the medical system 10, 101 to validate the combination of the medical probe 14, the medical device 12, a patient, and/or a mode of operation of the medical device 12, e.g., a procedure (therapy or monitoring).

If an inappropriate combination of medical probe 14 and medical device 12 is detected (e.g., a fetal sensor attached to an adult monitor (medical device), rather than a fetal sensor attached to a fetal monitor (medical device)), in Step 50 a message describing the violation is preferably written to the display 20 and/or an audible alarm is generated by the audio output 17. Functions of the medical device 12 related to this medical probe 14 are inhibited until another probe is connected to the monitoring device 12 (Step 42). This is an automation of the safety features provided by the auto-identification function(s).

Once the identifying data and other contents of the probe memory 26 of the medical probe 14 are verified, in Step 46 the medical device 12 reads the use value(s) from the probe memory 26 and preferably stores the use value(s) in internal memory 18 of the medical device 12. Optionally, the usage limit(s) of the usage criteria can also be read from the probe memory 26.

A possibility exists that the connection of the medical probe 14 with the medical device 12 may be interrupted during a single use, so in Step 46 a probe re-identification feature may be invoked. This interrupted use of the medical probe 14 can commonly occur for technical reasons, e.g., in order to move or assist the patient, or by accident. If included in the usage criteria for the probe 14 is a limitation on the number of uses, an interruption could pose a problem. To avoid the inconvenience of counting the resumption of use after such an interruption as a "new" use, in a preferred embodiment of the invention, a re-identification method may be provided in Step 46, further detailed in FIG. 3C.

Probe re-identification corresponds to a medical probe 14 being used in conjunction with a particular medical device 12, disconnected for a short time, and then reattached to either the same or another medical device 12. Even if the number of uses is not among the limitations on usage, the re-identification of a medical probe 14 by a different medical device 12 is important to the proper maintenance of patient data in the memory 18 of the medical device 12, as will be revealed below.

In Step 46.1 the date and time of last use ($P_{LU}$) are read from the medical probe 14 as part of the use value(s) retrieved in Step 46, and compared to the current date and time ($M_{CU}$) in the medical device 12. Various methods of representing time over a sufficient range (days to years) and with sufficient accuracy (seconds to minutes) and readily permitting arithmetic operations, such as comparison, are well known in the art. The interruption time, T, is computed in Step 46.1 as the difference $M_{CU}-P_{LU}$ with the assumption that the "clocks" of all medical devices 12 in use are consistent.

The interruption time T is compared in Step 46.2 with an interruption time limit (ITL), stored in either the medical probe memory 26 or the medical device memory 18. In one embodiment, if the currently attached probe was not last used within the interruption time limit (T>ITL), then a new use of the probe 14 must be counted. The logic for a new use of the probe 14 proceeds with the initial test of use values and establishment of "effective use" of the probe in Step 48, described below. In the preferred embodiment of a fetal sensor for oxygen saturation measurement, one hour is a suitable interruption time limit.

A negative value of T (T<0) is indicative of a mismatch between clocks in different medical devices 12. A small negative T may be treated as a zero result; a large negative magnitude would be interpreted as a usage criteria violation in Step 50. However, if the currently attached probe was last used within the interruption time limit (0<T≦ITL), then re-identification has been accomplished, and a new use is not counted. In a preferred embodiment, the medical device 12 may further compare the identifying data for the medical probe 14 with the identifying data for recently used medical probe(s) 14 stored in the medical device memory 18, as shown in Step 46.3. If a match is found, and the identified probe 14 is the last one used with this medical device 12, as determined in Step 46.4, then the same use of the probe immediately resumes at Step 52.

If this probe 14 is not the last one used with this medical device 12, or if this probe was never previously used with the medical device, then it is advisable to warn the operator that a probe and/or patient change has taken place. Preferably, the newly-connected medical device 12 warns, in Step 46.5, that the medical probe was previously connected to a different device by writing a message to the display 20 and/or generating an audible alarm by means of the audio output 17. This situation could occur if, for example, the medical device 12 is taken out of service and replaced with another unit (medical device) after effective use of the probe 14 has commenced. However, it could also take place if multiple probes attached to monitors (medical devices) on different patients, e.g., in a ward or nursery setting, were accidentally interchanged, making re-identification important for patient safety. In a preferred embodiment, in Step 46.5 an operator will indicate whether this is indeed a re-identified sensor, proceeding to Step 46.6, or a new use, proceeding with Step 48.

Prior to enabling functions of medical probe 14, the medical device 12 will preferably update the clinical data in the device memory 18 in Step 46.6. In a preferred embodiment, old clinical data in the memory 18 is archived and/or purged, and patient data including identifying data and clinical data stored in the probe memory 26 is transferred from the medical probe 14 to the memory 18 of the medical device 12, as shown in Step 46.6. This transfer is preferably conditioned upon use of security means to validate that the medical device's operator is authorized to obtain any confidential data from the probe 14, including, but not limited to patient identification data and clinical data.

In another preferred embodiment, the medical device 12 may further validate the re-identification of the probe 14 by comparison of patient identifying information read from both the probe memory 26 and the device memory 18. This may detect an attempt to reuse the probe 14 on a new patient without sufficient time for cleaning and/or sterilization.

In yet another preferred embodiment, the medical device 12 may in Step 46.6 read from the probe memory 26 the identifying data for a medical device 12 to which the medical probe 14 was previously connected. This identifying data can be used by the currently connected medical device 12 to request the transfer of stored patient data from the previously used medical device. The request may take the form of a message to medical personnel, or direct transfer via an electronic connection such as a network (not shown).

If re-identification is accomplished, the logic then proceeds directly to Step 52. Otherwise, if the auto-identification of probe and intended use is deemed acceptable, in Step 48 the use value(s) can then be compared to usage limit(s), in terms of either count, duration, shelf life, regulatory guidance limit (if any) or warranty period to verify that the use value associated with the medical probe 14 has not reached a usage limit value. If a use value is substantially equivalent to the corresponding usage limit, in Step 50 a violation message, describing the type of violation and indicating that a new probe is required, is preferably written to the display 20 and/or an audible alarm is generated by the audio output 17. In Step 42 functions of the medical device 12 related to this medical probe 14 are inhibited until another probe is connected to the medical device 12.

Note that Step 42, inhibition of functions related to the medical probe 14, may be implemented in a number of ways. Without affecting the probe, the firmware of the controller 16 can simply be programmed to not perform processing related to the probe's functions. Alternately, the medical device 12 can change the probe memory 26 of the medical probe 14 in order to prevent any future reading and/or writing therein. Lastly, the medical device 12 can disable the functionality of the sensor/effector 24 by physically changing the device. For example, in a pulse oximetry sensor, a fuse or fusible link may be placed in line with the connections to one or both of the LEDs 30. By applying a sufficiently high current, the controller 16 could thereby disable the pulse oximetry sensor.

If none of the "usage criteria" are violated, then in Step 52 the use value may be displayed on display 20. In some embodiments, regardless of whether any usage violation has occurred, the use value(s) are written to the display 20 by the controller 16 to alert medical personnel to the remaining usefulness of the probe 14 (Step 52). If the remaining usefulness is limited, this information helps an operator to determine whether to replace the medical probe 14 or proceed with the therapy or monitoring.

In some applications, where the probe memory 26 is a microcontroller, microprocessor, or other device with more advanced mathematical capabilities, the use value(s) can be maintained in the probe memory 26 and updated internally, without further interaction with the medical device 12, as long as power is applied to the medical probe 14.

After the use value is displayed in Step 52, the probe functions are enabled. From time to time, the medical device 12 will test whether the medical probe is still in use, Step 54, and determine whether the medical probe has been in effective use for a length of time sufficient to count as a "use".

The commencement of therapeutic or monitoring activity with the medical probe 14 is indicated by a start-of-usage event. Any signal normally used by the medical device 12 to begin the therapeutic or monitoring sequence associated with medical probe 14 can be used as the start-of-usage event, to commence updating the use value(s) in Step 56. Examples of suitable start-of-usage events are reading an activated pushbutton or other switching device indicating commencement of therapy reading an input signal from an external device, or, in some applications, connecting the medical probe 14 to the medical device 12.

The start-of-usage event will typically be conditioned upon completion of a minimal amount of effective use. For example, in an application where medical monitoring may be expected to go on for hours, it is reasonable to require a short period of effective monitoring (medical probe in place, signals received and interpretable, results displayed, etc.) prior to considering the monitoring "effective". This prevents the system from deducting a "use" from the life of a medical probe because it was briefly tested, inadvertently turned on, connected in order to cause display of the useful life left, or was demonstrated without actual clinical benefit. These events would not be considered an effective use, to update the use value(s) in Step 56. In a preferred embodiment in a pulse oximetry sensor, five minutes of successful monitoring of the oxygen saturation and pulse rate data is considered effective use to constitute a "use."

When the therapy or monitoring is deemed to have started, a date and time stamp, along with the identifying data of the medical probe 14, is preferably stored in the memory 18 of the medical device 12 (Step 56). A usage record consisting of the date and time stamp, along with the identifying data of the medical device 12, is preferably stored in the probe memory 26 of the medical probe 14. It will be obvious that the usage records can be stored either in the medical probe 14, the medical device 12, or both.

In Step 56 the use value is updated, e.g., a usage time limit is decremented, accordingly.

In Step 57, a comparison is made with the usage criteria and the updated use value(s) to determine if any usage criteria are violated. If no usage criterion is violated, then the probe use logic returns to Step 54, and the Steps 54–57 repeat until a usage criterion is violated or the probe is no longer in use. When a usage criterion is violated, e.g., the corresponding use value is equivalent to a predetermined value, in Step 58 a violation message is displayed and/or an audible alarm is made.

In applications where the usage criterion is duration of use, a timing function must be activated when the start-of-usage event occurs. Preferably, the controller 16 of the medical device 12 performs the timing function. Alternatively, in applications where the memory storage device 26 is a microcontroller or other device capable of providing a timing function, the timing function may be performed in the medical probe 14. When the duration of use of the medical probe 14 is substantially equivalent to a predetermined value, the controller 16 in the medical device 12 will preferably write a usage criterion violation message to the display 20 and/or generate an audible alarm by means of the audio output 17 (Step 58).

In applications where a usage criterion is a number of total uses, the use value must be changed only once for each therapeutic or monitoring sequence. When the use value reaches a predetermined number of uses, a message describing the usage criterion violation is preferably written to the display 20 of the medical device 12, and an audible alarm is generated by the audio output 17. Preferably, a warning will be written to the display 20 by the controller 16 prior to the last use, thereby allowing medical personnel to obtain a new probe for replacement. In some applications, a continual count may be maintained on the display 20 of the medical device 12. Once the use value has reached the usage limit value, the controller 16 in the medical device 12 will preferably write a usage criterion violation message to the display 20 and/or generate an audible alarm by means of the audio output 17 (Step 58).

Depending upon the type of medical probe 14, its mode of use by the medical device 12, and the usage criteria that has been violated, different actions may be selected when a usage violation occurs. After the violation message has been displayed and/or the audible alarm made, in Step 58, further function of the medical probe 14 may be immediately inhibited, or permitted to continue.

If the medical probe 14 is permitted to continue to be used, then the invention repeats Steps 54–59, e.g., a determination is again made in Step 54 as to whether the medical probe 14 is in use, etc. If the function is not allowed to continue in Step 59, processing will proceed to step 62, wherein the invention will update the memory 18 of the medical device 12 and/or the probe memory 26 of the medical probe 14, storing the use value, date and time stamp the use and then proceeding to Step 42 to inhibit the medical probe to function. Specifically, in some embodiments of the invention, especially those in which a time duration limit is employed (e.g., duration of delivery of a drug dose), the medical device 12 will immediately inhibit function Step 42 until the medical probe 14 is replaced (Step 38).

In other embodiments, especially those in which the usage limit is based upon the number of uses of the medical probe 14, it is permissible to finish the current treatment or monitoring operation. Prior to beginning another use of the same medical probe 14, however, the medical device 12 will, in Step 46, read the use value and will not allow another therapeutic or monitoring usage to begin until the medical probe 14 is replaced. Again, the timing function can be operated to count either up to a known value, or down from an initial value to zero. Although changing the use value from an initial use number has been described in terms of decrementing, it will be apparent to one of ordinary skill in the art that the medical system 10 could be easily modified to increment, decrement, or use an apparent random sequence.

Periodically during use of the medical probe 14, a date and time stamp, along with the identifying data of the medical probe 14, is preferably updated in the memory 18 of the medical device. This data can be used in conjunction with clinical logs to track the identity of the equipment and the personnel that were involved in a given monitoring procedure. Likewise, usage is preferably periodically updated in the probe memory 26 of the medical probe 14. Although this storage of usage records could be done only when the therapy or monitoring ends (Step 62), it may be possible to shut off the medical system 10, or disconnect the medical probe 14, preventing the usage data from being recorded. This is a form of tampering with usage data.

Therefore, in a preferred embodiment, a full usage record of date and time stamp, along with the identifying data of the medical device 12, is written to the medical probe 14 when effective usage is confirmed. Thereafter, at periodic time intervals during continued use, a bit is written in the probe memory 26 to keep an approximate record of duration of use. Preferably the periodic time interval is an hour, however the periodic time interval may be shorter, e.g., a second. Typically, the medical device 12 contains non-volatile RAM used to hold the current usage data, and this may be updated much more frequently, e.g., every second.

In some applications, the medical device 12 may include input devices such as keyboards, bar code readers, biometric scanners, serial links, and other communication devices, for logging the identity of clinicians and the patient involved in a procedure, thereby providing a complete log for later review.

In a preferred embodiment, radio frequency identification functions can be incorporated in the medical device 12 to identify medical personnel, patients, and other data. Preferably, date and time stamps, identifying data of the medical device 12, and other identifying data is stored in both the probe memory 26 of the medical probe 14 and the memory 18 of the medical device 12 as a cross check. Storing this data in both locations simplifies the process of later identifying the equipment used in a given monitoring process in the event of a failure. In some applications, detailed data regarding medical parameters encountered in a given procedure may be stored. Alternatively, the controller 16 may check for defined errors or conditions and store data when such conditions occur.

Although storing usage, date and time stamp data at the beginning of effective use and periodically during the function of the medical system 10 has been described, it will be apparent to one of ordinary skill in the art that this step could also be taken at the beginning of effective use, after the occurrence of predefined conditions, in the event of a system failure, at the end of use, in combinations, or in a number of other ways.

Although a distinct functional block diagram has been shown in FIGS. 3A, 3B and 3C, it will be apparent to one of ordinary skill in the art that changes in the order of certain functions, modifications of functions, and additions could be made without departing from the invention.

As noted above, in one highly preferred embodiment of the invention, an add-only memory (AOM) is used as the probe memory 26. One suitable device is the DS2502, manufactured by Dallas Semiconductor, Inc. The data sheet for this component, as published by Dallas Semiconductor, is incorporated herein by reference. This device contains a factory-written registration number plus multiple pages of user-programmable memory. The registration number contains a unique code for the customer (in this case, the manufacturer of the medical probe); a serial number; plus a CRC for validating the integrity of the data. The user-programmable memory can be written once, one bit at a time, and pages can be individually write-protected after programming to prevent modification.

Another advantage of the DS2502 is its incorporation of the 1-Wire™ multi-drop communications scheme, serving as the probe communications port 27. This method requires only a ground connection and second connection to supply power to the DS2502 as well as perform bi-directional communication. Since the ground connection may be connected to a common ground with other electrical functions in the medical probe, only one additional connection to the medical probe 14 is required.

Referring to FIGS. 1 and 2, the medical device 12 includes a device (host) communications port 19 consisting of appropriate hardware and software to interface to the probe memory 26. A suitable implementation of the 1-Wire™ interface is the DS2480 Serial Wire™ Line Driver, also manufactured by Dallas Semiconductor, Inc. The data sheet for this component, as published by Dallas Semiconductor, is incorporated herein by reference. This device interfaces to the controller 16 via a standard UART, or serial interface. Generally, the firmware of the controller 16 must include the ability to operate the device (host) communication port 19, send commands to the probe communication port 27 to read and write the probe memory 26; interpret status information from the host communication port 19, the probe communication port 27, and the probe memory 26; and complete the security function including the keys required by the encryption system used to secure communications and the ability to update the use values.

Figure 4:
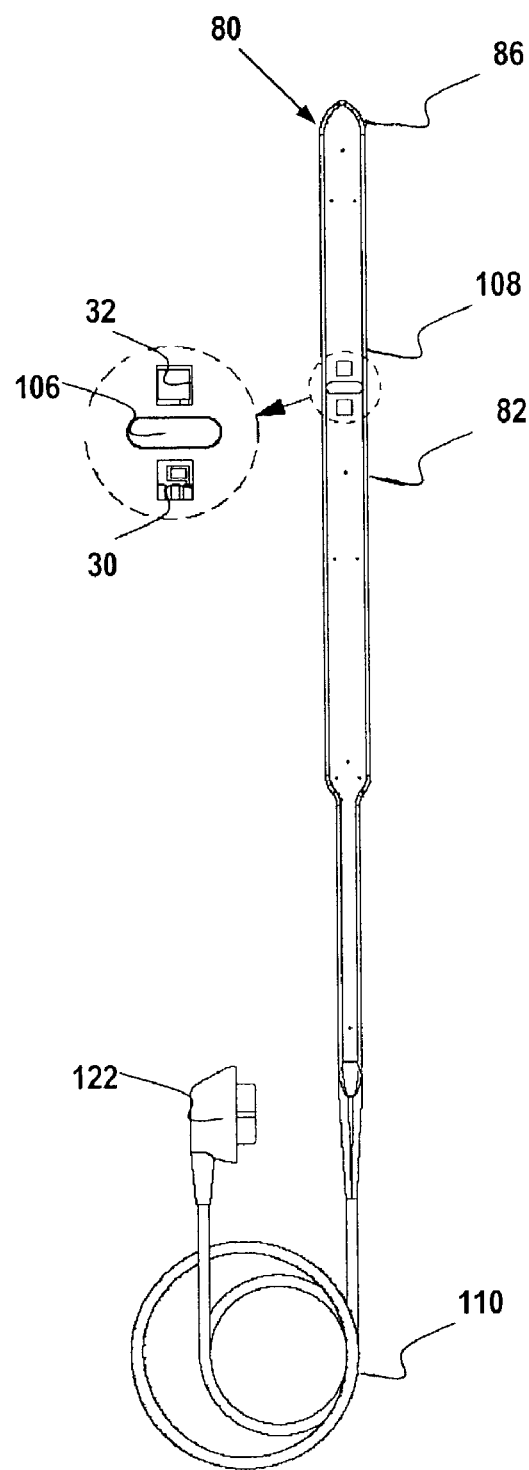
FIG. 4 is a fetal sensor for use with a medical device of the medical monitoring system of FIGS. 2 and 3 of the present invention.

The problems associated with prior art medical devices are particularly acute in fetal monitoring devices, due to the internal placement of sensors and conditions surrounding perinatal monitoring. Consequently, in a highly preferred embodiment of the present invention, the medical probe 14 comprises a fetal sensor 80 for monitoring the oxygen saturation and/or other medical parameters in utero, as can be seen in FIG. 4. An example of a fetal oxygen sensor is more fully described in U.S. Pat. No. 5,425,362, which is incorporated herein by reference. The fetal sensor 80 includes a flexible housing 82 and a soft molded tip 86. Preferably the soft molded tip 86 is integrally coupled to the remainder of the fetal sensor 80. The flexible housing 82 and the soft molded tip 86 help minimize the possibility of membrane rupture or tissue damage. The fetal sensor 80 includes a flexible strip, such as spring steel (not shown) coated with a smooth surfaced covering (such as a silicone rubber, thermoplastic elastomer (TPE), or Teflon).

The fetal sensor 80 can include preferably one or more of a variety of sensors, such as a pressure sensor, an ECG sensor, an EEG sensor, a temperature sensor, an oxygen sensor, an ultrasound transducer/sensor, a laser diode emitting IR signals with an associated detector, and/or a chemical sensor. In some applications, the fetal sensor 80 can include a balloon type device that can be inflated to variable pressures and used with conventional feed back electronics to maintain a substantially constant pressure of engagement of the device with at least one of the fetus and the uterus of the mother.

In a preferred embodiment, shown in FIGS. 2 and 4, sensor 24 is preferably the fetal sensor 80. Fetal sensor 80 includes a pulse oximetry sensor 108, which generally comprises two or more light emitting devices 30 (e.g., LEDs) of varying wavelengths, and one or more photodetector(s) 32. A light blocker 106 ensures that light passes through the fetal tissue rather than directly from the emitters to the detectors. Relative intensity of the light backscattered from the fetal tissue at different wavelengths is used to calculate oxygenation levels in ways known in the art.

Also, in the preferred embodiment, shown in FIG. 2, the medical device 12 comprises an oximeter for calculating the oxygenation ($SpO_2$) level. One particular example of a pulse oximeter is described in U.S. Pat. No. 6,163,715 B1, issued to Larsen et al., which disclosure is incorporated by reference herein. The fetal pulse rate may also be derived from the detected signals of the fetal sensor 80, as revealed in U.S. Pat. No. 6,339,715.

Referring again to FIGS. 2 and 4, all of the connections of the fetal sensor 80 are routed via a cable 110 to a single connection point with the medical device 12. In a preferred embodiment, the connection point comprises a connector 122 that couples to a mating connector of the medical device 12. The probe memory 26 is preferably embedded in the connector 122 to limit the overall size of the medical probe 14 and reduce the risk of tampering. The medical device 12 preferably provides power for the medical probe 14.

The medical device 12 is in this preferred embodiment a fetal pulse oximeter. The start-of-usage event is conditioned upon the fetal sensor 80 being connected and in place, yielding signals that result in successful monitoring of oxygen saturation and pulse rate for at least five minutes. At that time and every hour thereafter, a usage record is written to the probe memory 26 as long as the fetal sensor 80 remains attached the medical device 12 and the pair remain in use.

Although in the preferred embodiment the connector 122 has been shown for handling electrical signals, it will be apparent to one of ordinary skill in the art that infrared, radio frequency or fiber optic connections, or some combination of means, could be utilized with appropriate rearrangement of illustrated components without departing from the invention.

Figure 5:
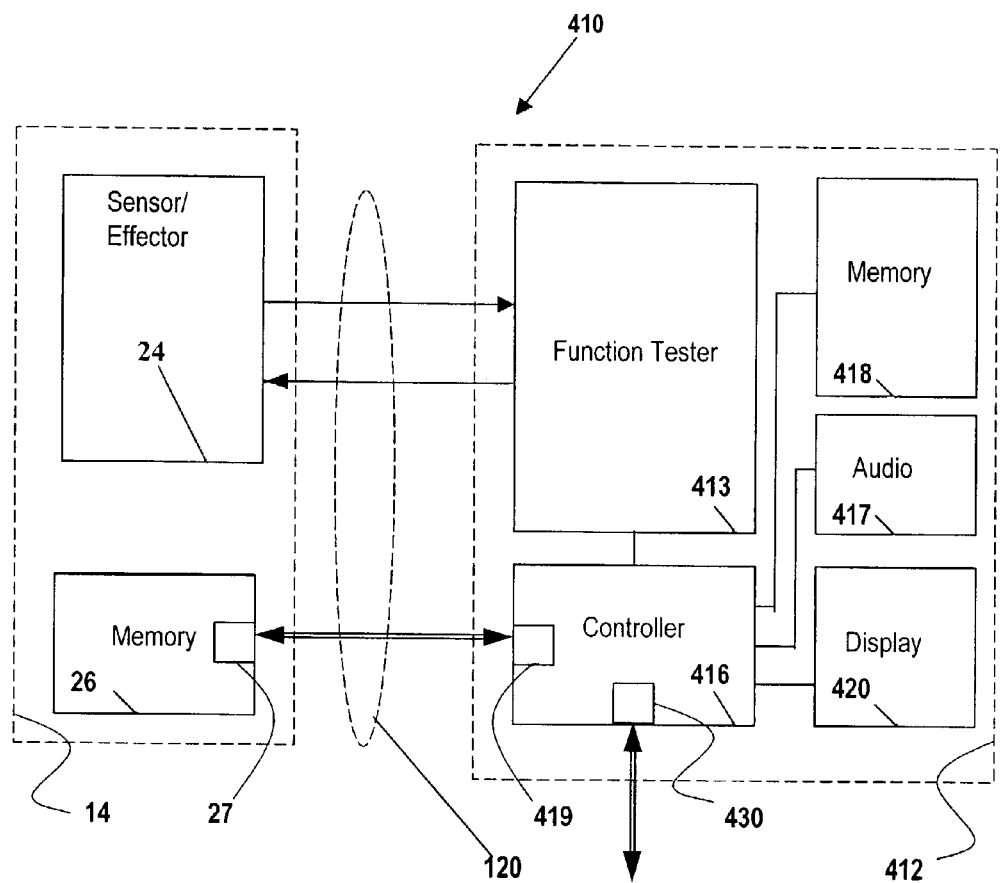
FIG. 5 is a block diagram of a medical reprocessing system constructed in accordance with the present invention.
Figure 6:
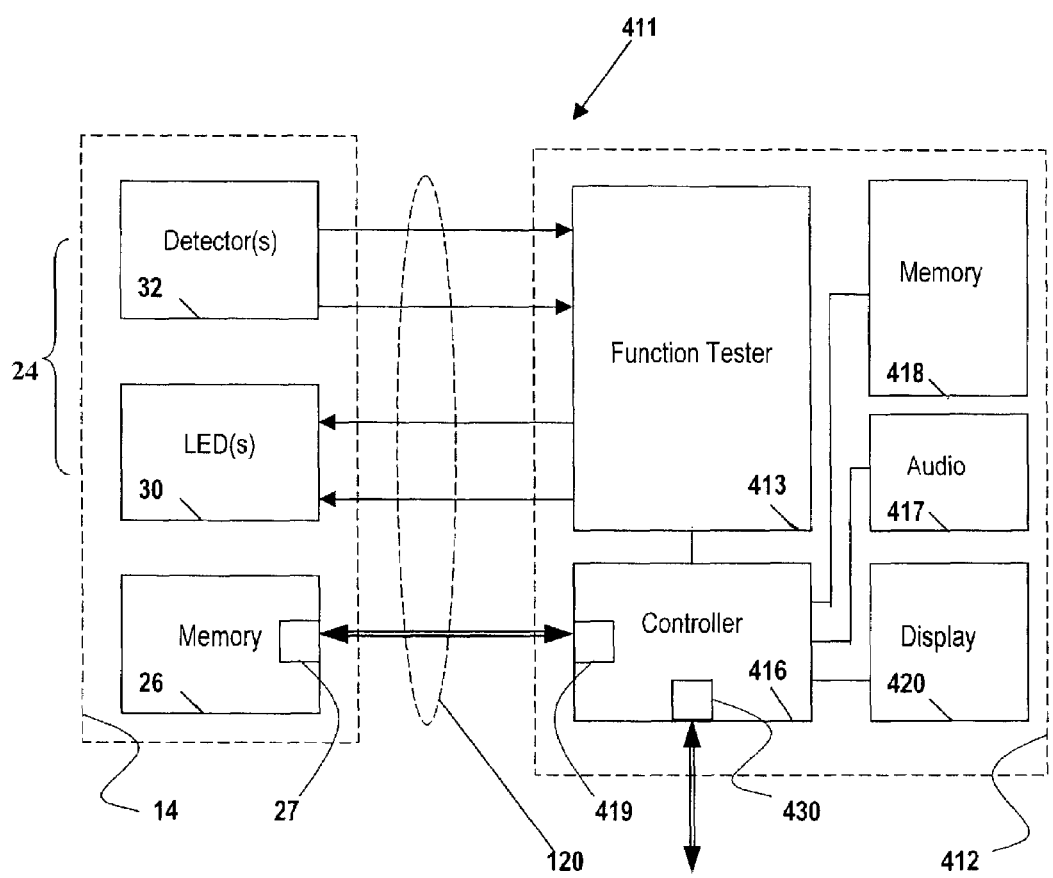
FIG. 6 is a block diagram of a medical reprocessing system constructed in accordance with a preferred embodiment of the present invention.

In FIG. 5, another embodiment of the present invention, a medical reprocessing system 410 is shown. The medical reprocessing system 410 includes a medical probe 14 attached to a medical reprocessor 412 via an external connection 120. The medical probe 14 that has been disabled as a result of usage criteria violation(s) is shown attached to the medical reprocessor 412. In FIG. 6, a preferred medical reprocessing system 411, is shown having a medical probe 14, where the medical probe 14 is preferably a pulse oximetry sensor. The medical probe 14 of FIG. 5 may be any of the previously discussed herein medical probes, having an effector/sensor 24, a probe memory 26, and an external connection configured for transferring data between the medical reprocessor 412 and the probe 14. The external connection may be connection 120 previously described herein, or a unique connection may be employed foi reprocessing, without loss of generality. The medical reprocessor 412, shown in FIGS. 5 and 6, consists of a controller 416, a memory 418, a reprocessor communication port 419, a function tester 420, and an external connection means 430. A function tester establishes whether the sensor(s) and effector(s) 24 of the medical probe 14 are functioning within normal operating limits, verifying, e.g., signal strength and signal to noise ratio of sensor(s) and current draw of effector(s).

Figure 7:
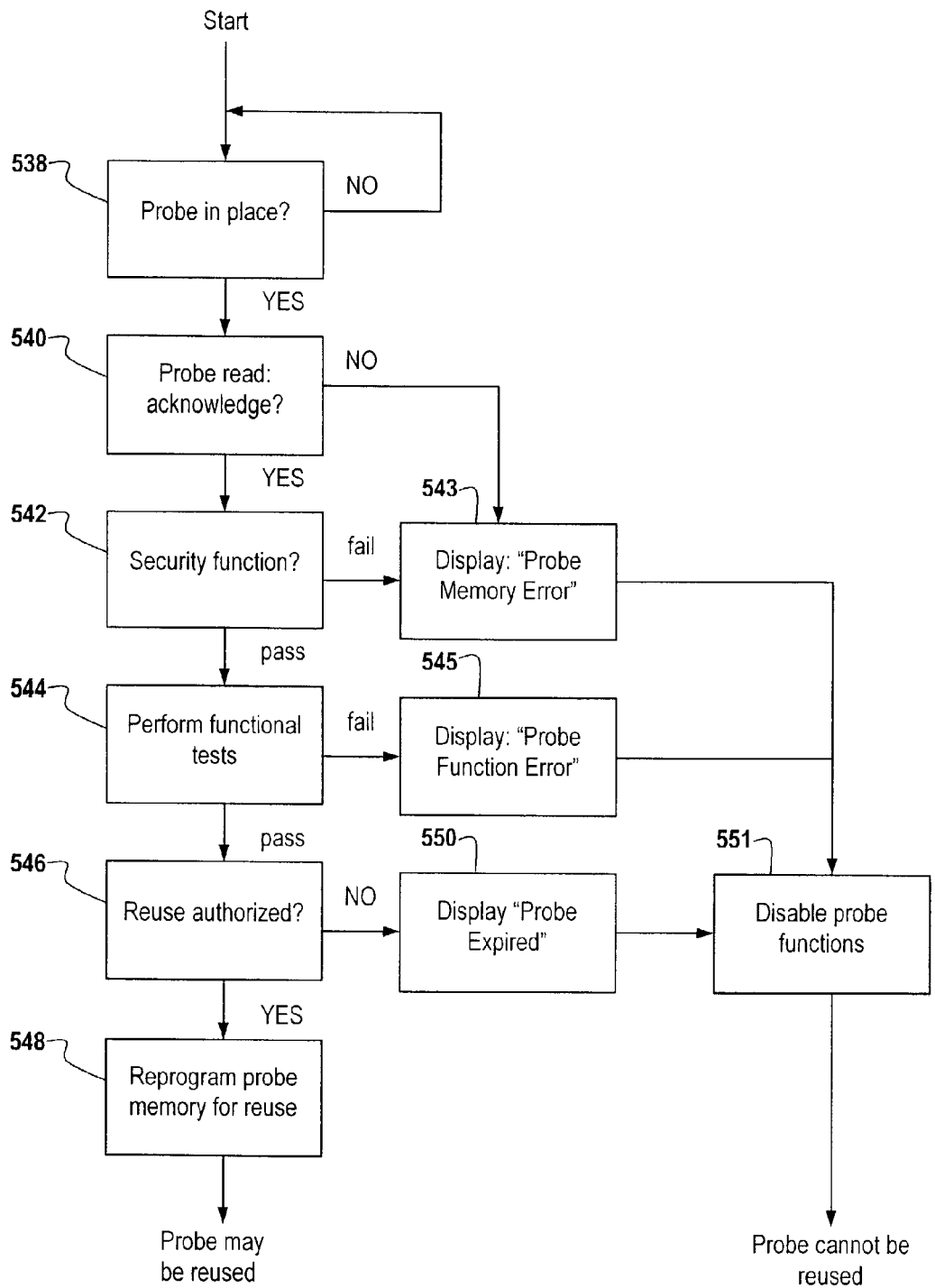
FIG. 7 is an operational block diagram of the medical reprocessing system of FIGS. 5 and 6 constructed in accordance with the present invention.

FIG. 7 is an operational block diagram of the medical reprocessing system 410, 411 as shown in FIGS. 5 and 6. The medical reprocessing system 410 or 411, performs security function(s) and functional testing to determine whether reuse of the medical probe is authorized. In Step 538, a medical probe 14 is detected to be attached to the reprocessor 412.

In Step 540, the reprocessor 412 attempts to read the contents of the probe memory 26 through the reprocessor communication port 419 in connection with the probe communication port 27 via a "Read Request" and detects an "acknowledge" from the probe memory 26. If the medical probe 14 is damaged or the probe memory 26 is incorrectly programmed, the medical probe 14 will not acknowledge the read request and in Step 543 the display 420 will display a message "Probe Memory Error". Thus, in Step 540 and 543, a medical probe with a damaged probe memory or with incorrectly programmed probe memory is rejected as unusable. In Step 542, a security function is run on the probe 14 as described previously herein. If the medical probe 14 fails the security function, then the display message is "Probe Memory Error."

In Step 544, the controller 416 directs functional tests of the medical probe 14. The functional testing of Step 544 may include verifying that: the sensor(s) and/or effector(s) in the medical probe 14 are operating within design parameters; the physical integrity of the medical probe 14 is adequate (e.g., surface testing for cracks); and/or determining the efficacy of cleaning and sterilization (e.g., evaluation of biological indicators, surface examination for contaminants, etc.). If the medical probe 14 fails functional tests, in Step 545 the display 420 displays a message "Probe Function Error".

In Step 546 the controller 416 seeks reuse authorization for reprocessing of the medical probe 14. The reuse authorization of Step 546 may be a local function in the form of an algorithm run by the controller 416, evaluating usage history, functional testing, and other data. Alternately, the reuse authorization step may depend upon a security code, manually entered by an operator, or obtained in a transaction with a remote party via the external connection means 430. In yet another alternate embodiment, the entire reuse authorization step may be performed by a remote party supplied the usage history and functional testing data via the external connection 430, and returning a reuse authorization decision. The external connection 430 may be telephonic, cable, radio frequency, or other technology. In a preferred embodiment, the controller 416 utilizes standard Internet technology to pass transactions reliably and securely to a remote reuse authorization party over the external connection 430. Reuse authorization may include assessment of licensing fees related to reprocessing of the medical probe 14.

If reuse authorization in Step 546 is refused, then in Step 550, the display 420 displays a message that the "Probe Expired." The probe function is disabled in Step 551 and the medical probe 14 cannot be reused.

If the authorization for reuse is granted in Step 546, then in Step 548, the probe memory 26 is modified to permit further use of the medical probe 14. The modification of the probe memory 26 may include data changes, such as resetting the date of manufacture to represent the date of reprocessing (extending shelf and warranty life); clearing the duration of use value; zeroing the count of uses; and so forth. Additionally, usage criteria data stored in the probe memory 26 may be modified to reflect a change in condition of the medical probe 14. To protect the privacy of patient data, in a preferred embodiment all patient-specific data, including patient and caregiver identification, clinical data, procedures, physiological data, and timestamps thereof, are deleted from the probe memory 26.

If in Steps 543, 545, or 550 a medical probe 14 fails reprocessing for any reason, in Step 551, the medical probe 14 may be disabled to prevent further attempts at use. Disabling the probe functions consist of at least removal of any patient-specific data from the probe memory 26. In a preferred embodiment, the probe memory 26 may be locked to prevent any further write operations to it. Preferably, the functions of the sensor/effector(s) 24 are directly disabled, as suggested above for the case of a pulse oximetry sensor, for example by opening a fuse or fusible link with a sufficiently high electrical current.

In a preferred embodiment shown in FIG. 6, the medical reprocessing system 411 is designed for use with a medical probe 14 that is a pulse oximetry sensor, such as fetal sensor 80 of FIG. 4 for performing fetal pulse oximetry. The function tester 413 provides means to sense open and short circuits in the medical probe 14, evaluate current draw and light output of the light emitting device(s) 30, sensitivity and noise of the photodetector(s) 32, and perform other tests.

While preferred embodiments have been illustrated and described, it should be understood that changes and modifications can be made thereto without departing from the invention in its broadest aspects. Various features of the invention are defined in the following claims.

What is claimed is:

1. A method for limiting the use of a medical probe according to a set of usage criteria using a security function, the method comprising the following steps:
   (a) coupling a probe memory to a medical probe, the probe memory having an identifying data about the medical probe, therein;
   (b) coupling the medical probe to a medical device;
   (c) coupling the medical probe to a patient;
   (d) retrieving a set of use values associated with use of the medical probe from the probe memory;
   (e) using a security function to verify that the contents of the probe memory have not been corrupted or tampered with;
   (f) applying a set of usage criteria periodically during use of the medical probe, comprising repetition of the following steps:
      (i) updating the set of use values of the medical probe during use and creating an updated set of use values;
      (ii) testing the updated set of use values against the set of usage criteria related to the medical probe;
      (iii) performing an expiration response when one or a combination of the usage criteria are violated;
      (iv) storing the updated set of use values on a periodic basis in the probe memory;
   (g) retrieving and storing the identifying data about the medical probe from the probe memory, and storing the data in a memory component of the medical device;
   (h) storing a time and date stamp of the use of the medical probe memory in a memory component of the medical device;
   (i) comparing the identifying data about the medical probe, read from the probe memory, with the identifying data and time and date stamp of the use(s) corresponding to a previously coupled medical probe(s) as stored in the medical device memory; and including determining whether an interrupted usage of the medical probe has resumed, or a new usage of the medical probe has begun.

2. The method as defined in claim 1, wherein Step (e), the security function includes a physical security method, or an algorithmic security method, or both.

3. The method as defined in claim 2, wherein the physical security method includes a portion of the probe memory that is a write-once memory device.

4. The method as defined in claim 2, wherein the algorithmic security function includes a data encoding system with encryption:
   in the medical device for encrypting data before it is stored in the probe memory, and for decrypting data read from the probe memory in the medical device; or
   in the medical probe for encrypting data from the medical device in the probe memory when it is stored therein, and for decrypting data stored in the probe memory when it is read by the medical device;
   or in both.

5. The method as defined in claim 4, wherein the data encoding system incorporates symmetrical encryption or wherein the data encoding system incorporates asymmetrical encryption.

6. The method as defined in claim 5, wherein the data encoding system incorporates public key encryption.

7. The method as defined in claim 1, wherein the probe memory contains the set of usage criteria.

8. The method as defined in claim 1, further comprising the step of retrieving the set of usage criteria from the probe memory.

9. The method as defined in claim 1, wherein the Step (f) set of usage criteria includes one or more of the following:
   a) a duration of use of the medical probe in conjunction with the medical device or other medical devices; or
   b) a count of the number of uses of the medical probe in conjunction with the medical devices or with the other medical devices; or
   c) an elapsed time since manufacture or reprocessing of the medical probe.

10. The method as defined in claim 1, wherein Step (f), the expiration response includes one or more of the following steps:
    a) displaying a message indicating that a new medical probe is required; or
    b) modifying the medical probe to disable a therapeutic function(s) and/or a monitoring function(s) of the medical probe after the present use; or
    c) immediately disabling the therapeutic and/or monitoring function(s) of the medical device related to the medical probe.

11. The method as defined in claim 10, wherein Step 47b, further comprises the step of causing a fuse or fusible link in the circuitry of the medical probe to open, thereby disabling the therapeutic and/or monitoring function(s) of the medical probe.

12. The method as defined in claim 1, wherein the medical probe is a pulse oximetry sensor.

13. The method as defined in claim 1, wherein the medical probe is a fetal sensor.

14. A method for limiting the use of a medical probe according to a set of usage criteria using a security function, the method comprising the following steps:
    (a) coupling a probe memory to a medical probe, the probe memory having an identifying data about the medical probe, therein;
    (b) coupling the medical probe to a medical device;
    (c) coupling the medical probe to a patient;
    (d) retrieving a set of use values associated with use of the medical probe from the probe memory;
    (e) using a security function to verify that the contents of the probe memory have not been corrupted or tampered with;
    (f) applying a set of usage criteria periodically during use of the medical probe, comprising repetition of the following steps:
       (i) updating the set of use values of the medical probe during use and creating an updated set of use values;
       (ii) testing the updated set of use values against the set of usage criteria related to the medical probe;
       (iii) performing an expiration response when one or a combination of the usage criteria are violated;
       (iv) storing the updated set of use values on a periodic basis in the probe memory;

(g) storing a time and date stamp of the use of the medical probe memory in the probe memory, and storing identifying data about the medical device in the probe memory; and (h) comparing the stored medical device identifying data, read from the memory component of the medical device, to identifying data and time and date stamp of use(s) corresponding to previously coupled medical device(s) as read from the probe memory; and including determining whether an interrupted usage of the medical probe with the medical device has been resumed, or a new usage of the medical probe has begun.

15. A method for limiting the use of a medical probe according to a set of usage criteria using a security function, the method comprising the following steps:

(a) coupling a probe memory to a medical probe, the probe memory having an identifying data about the medical probe, therein;

(b) coupling the medical probe to a medical device;

(c) coupling the medical probe to a patient;

(d) retrieving a set of use values associated with use of the medical probe from the probe memory;

(e) using a security function to verify that the contents of the probe memory have not been corrupted or tampered with; and (f) applying a set of usage criteria periodically during use of the medical probe, comprising repetition of the following steps:

(i) updating the set of use values of the medical probe during use and creating an updated set of use values;

(ii) testing the updated set of use values against the set of usage criteria related to the medical probe;

(iii) performing an expiration response when one or a combination of the usage criteria are violated;

(iv) storing the updated set of use values on a periodic basis in the probe memory;

(v) (performing an auto identification function, including comparing the medical probe type, the medical device, a patient, and a mode of operation of the medical device to verify that the mode of operation of the medical device is permitted when applying the medical probe to the patient.

16. A method for limiting the use of a medical probe according to a set of usage criteria using a security function, the method comprising the following steps:

(a) coupling a probe memory to a medical probe, the probe memory having an identifying data about the medical probe, therein;

(b) coupling the medical probe to a medical device;

(c) coupling the medical probe to a patient;

(d) retrieving a set of use values associated with use of the medical probe from the probe memory;

(e) using a security function to verify that the contents of the probe memory have not been corrupted or tampered with;

(f) applying a set of usage criteria periodically during use of the medical probe, comprising repetition of the following steps:

(i) updating the set of use values of the medical probe during use and creating an updated set of use values;

(ii) testing the updated set of use values against the set of usage criteria related to the medical probe;

(iii) performing an expiration response when one or a combination of the usage criteria are violated;

(iv) storing the updated set of use values on a periodic basis in the probe memory; and (g) storing a functional test sequence in the probe memory; storing a set of function test results in the probe memory; activating the medical probe to perform the functional test sequence and gathering results of the functional test sequence; comparing results of the functional test sequence with the stored set of function test results and reporting the results of the functional test sequence.

17. A method for limiting the use of a medical probe according to a set of usage criteria using a security function, the method comprising the following steps:

(a) coupling a probe memory to a medical probe, the probe memory having an identifying data about the medical probe, therein;

(b) coupling the medical probe to a medical device;

(c) coupling the medical probe to a patient;

(d) retrieving a set of use values associated with use of the medical probe from the probe memory;

(e) using a security function to verify that the contents of the probe memory have not been corrupted or tampered with;

(f) applying a set of usage criteria periodically during use of the medical probe, comprising repetition of the following steps:

(i) updating the set of use values of the medical probe during use and creating an updated set of use values;

(ii) testing the updated set of use values against the set of usage criteria related to the medical probe;

(iii) performing an expiration response when one or a combination of the usage criteria are violated;

(iv) storing the updated set of use values on a periodic basis in the probe memory; and (g) storing identifying information and demographic information about the patient coupled to the medical probe in the probe memory.

18. A method for limiting the use of a medical probe according to a set of usage criteria using a security function, the method comprising the following steps:

(a) coupling a probe memory to a medical probe, the probe memory having an identifying data about the medical probe, therein;

(b) coupling the medical probe to a medical device;

(c) coupling the medical probe to a patient;

(d) retrieving a set of use values associated with use of the medical probe from the probe memory;

(e) using a security function to verify that the contents of the probe memory have not been corrupted or tampered with;

(f) applying a set of usage criteria periodically during use of the medical probe, comprising repetition of the following steps:

(i) updating the set of use values of the medical probe during use and creating an updated set of use values;

(ii) testing the updated set of use values against the set of usage criteria related to the medical probe;

(iii) performing an expiration response when one or a combination of the usage criteria are violated;

(iv) storing the updated set of use values on a periodic basis in the probe memory; and (g) storing a set of therapeutic and monitoring results associated with the patient in the probe memory.

19. A method for limiting the use of a medical probe according to a set of usage criteria using a security function, the method comprising the following steps:

(a) coupling a probe memory to a medical probe, the probe memory having an identifying data about the medical probe, therein;

(b) coupling the medical probe to a medical device;

(c) coupling the medical probe to a patient;

(d) retrieving a set of use values associated with use of the medical probe from the probe memory;

(e) using a security function to verify that the contents of the probe memory have not been corrupted or tampered with;

(f) applying a set of usage criteria periodically during use of the medical probe, comprising repetition of the following steps:
  (i) updating the set of use values of the medical probe during use and creating an updated set of use values;
  (ii) testing the updated set of use values against the set of usage criteria related to the medical probe;
  (iii) performing an expiration response when one or a combination of the usage criteria are violated;
  (iv) storing the updated set of use values on a periodic basis in the probe memory; and (g) transmitting a query signal from the medical device to the medical probe and waiting for an acknowledge signal from the medical probe device prior to beginning the therapeutic or monitoring function of the medical probe.

* * * * *

UNITED STATES PATENT AND TRADEMARK OFFICE
CERTIFICATE OF CORRECTION

PATENT NO. : 7,048,687 B1
APPLICATION NO. : 10/361167
DATED : May 23, 2006
INVENTOR(S) : James L. Reuss It is certified that error appears in the above-identified patent and that said Letters Patent is hereby corrected as shown below:

On Title Page, Item (63), should read, in the Related U.S. Application Data: "Continuation-in-part of application No. 10/045,475, filed on Oct. 22, 2000, now abandoned, which is a continuation of application No. 09/291,769, filed on Apr. 14, 1999, now Pat. No. 6,308,089," should be - -Continuation-in-part of application No 10/045,475, filed on Oct. 22, 2001, now abandoned, which is a continuation of application No. 09/291,769, filed on Apr. 14, 1999, now Pat. No. 6,308,089.- -

On column 22, line 32, in Claim 11, "47b" should read - -10b- -.

Signed and Sealed this

Fifteenth Day of August, 2006

JON W. DUDAS
*Director of the United States Patent and Trademark Office*